United States Patent [19]

Brault

[11] Patent Number: 4,506,664

[45] Date of Patent: Mar. 26, 1985

[54] SPINEBOARD

[76] Inventor: Richard A. Brault, 17 Pembroke St., Apt. 11, Toronto, Ontario, Canada, M5A 2N6

[21] Appl. No.: 480,340

[22] Filed: Mar. 30, 1983

[51] Int. Cl.³ .............................................. A61F 5/04
[52] U.S. Cl. ..................................... 128/134; 5/82 R
[58] Field of Search .................. 128/134, 84 R, 84 C, 128/85, 87 R, 75; 5/82 R

[56] References Cited

U.S. PATENT DOCUMENTS

| 2,675,564 | 4/1954 | Hughes | 128/134 X |
| 3,063,447 | 11/1962 | Kirsten | 128/134 |
| 3,650,523 | 3/1972 | Darby, Jr. | 128/134 X |
| 3,732,863 | 5/1973 | Harrington | 128/84 C |
| 3,892,399 | 7/1975 | Cabansag | 128/134 X |
| 4,024,861 | 5/1977 | Vincent | 128/87 R |

Primary Examiner—John D. Yasko
Attorney, Agent, or Firm—Fetherstonhaugh & Co.

[57] ABSTRACT

A spineboard for immobilizing a prostrate patient comprises a body supporting board having a body restraint harness which consists of two lengths of flexible material each having a proximal end retained on the board at or adjacent the center of the width thereof. Each length of the harness has a sufficient extent to extend from the proximal end in a first direction around to the body of the patient to be secured to the board adjacent a side edge of the board remote from the proximal end. The body restraint harness is slidably mounted on the board so as to be positionable at any required point along the length of the patient. The body restraint harness also includes a shoulder harness and a head harness for immobilizing the patient. To facilitate the mounting and release of the distal end of each length of the harness, the side edges of the board are formed with a mounting edge over which hooks located at the end of the harness may hook. The board is formed with buoyancy compartments which serve to make the board horizontally buoyant in water.

13 Claims, 7 Drawing Figures

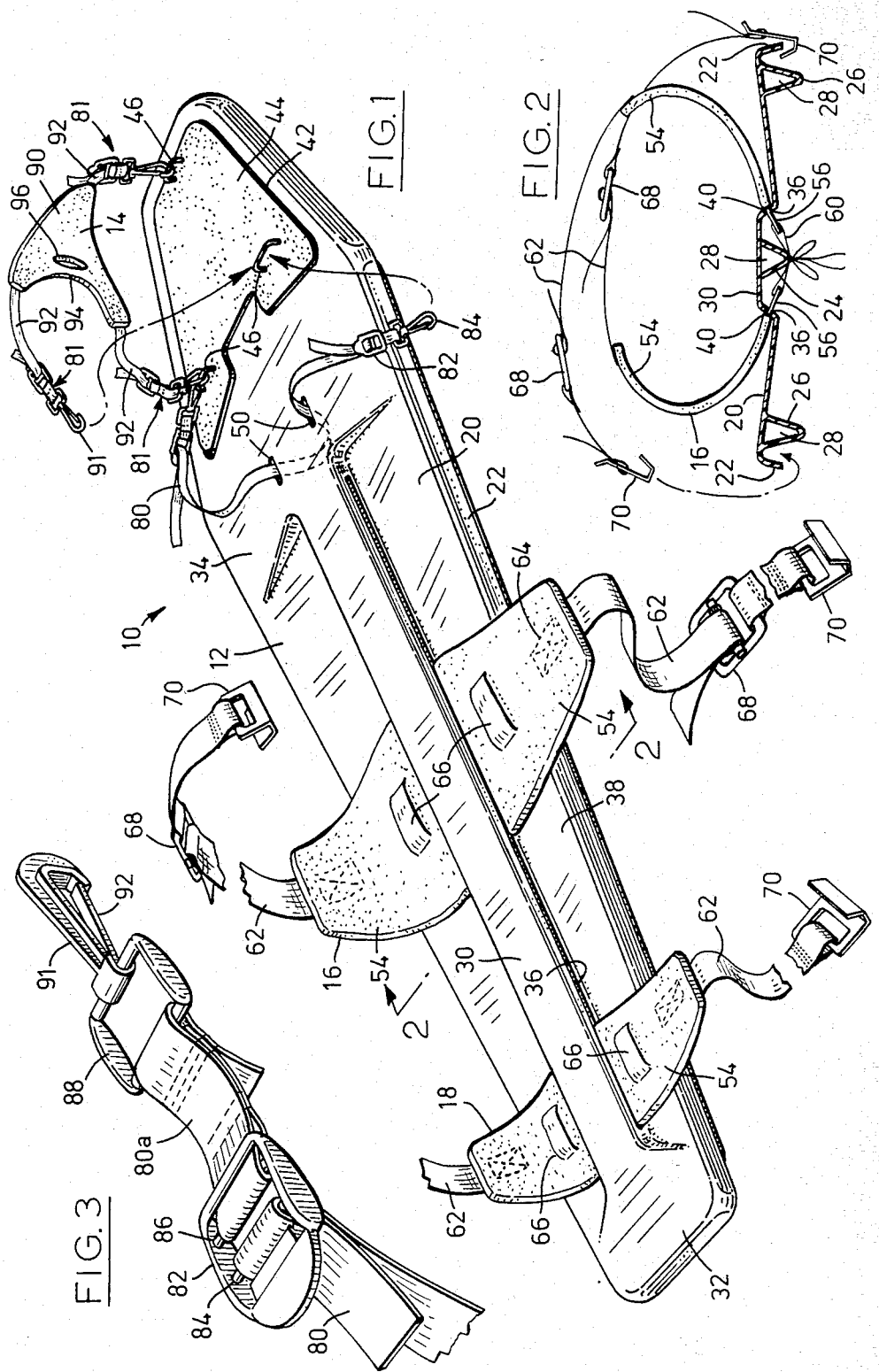

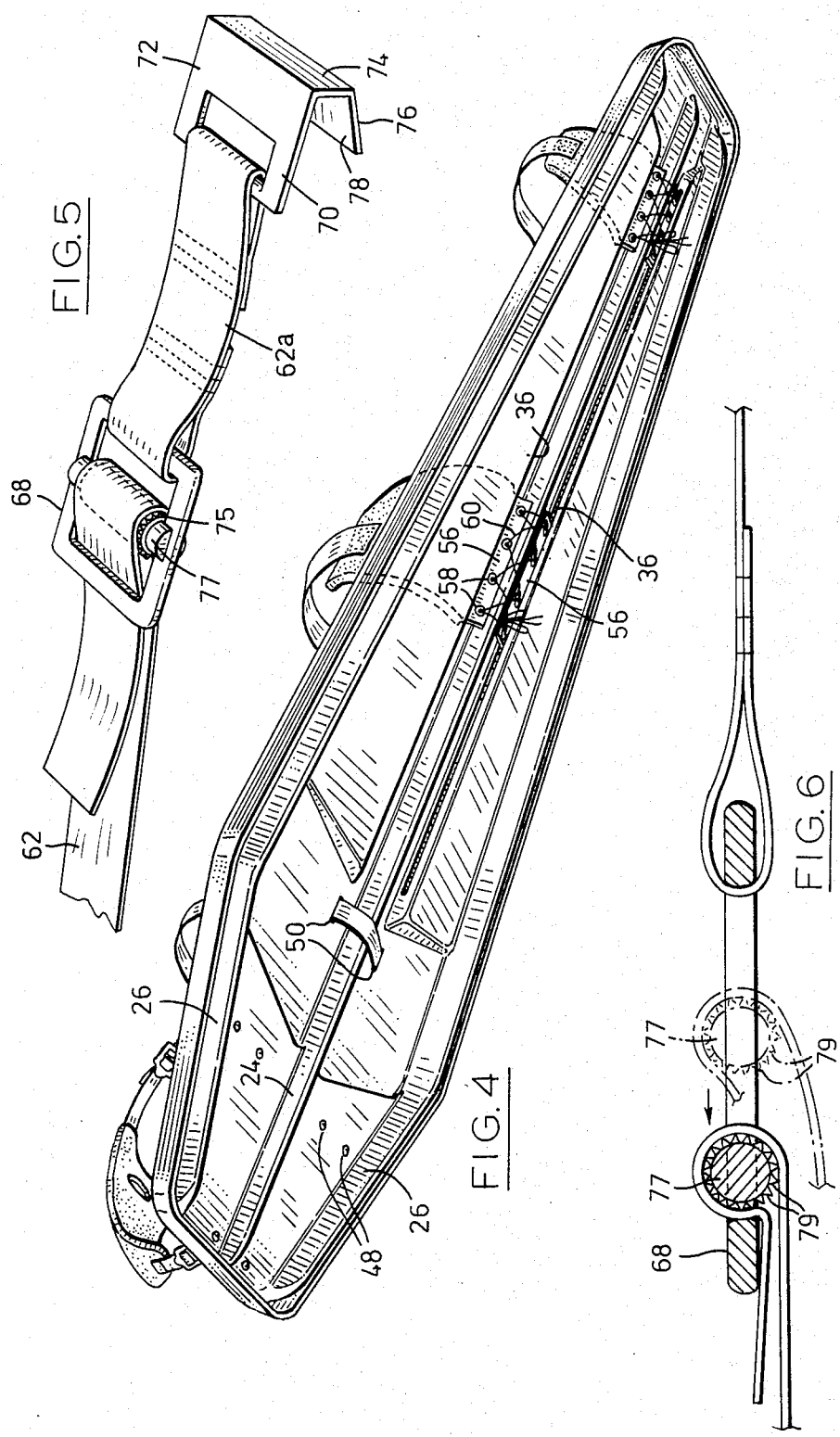

SPINEBOARD

This invention relates to spineboards. In particular, this invention relates to a buoyant aquatic spineboard.

PRIOR ART

A spineboard is a form of a rigid stretcher which is used for the purposes of supporting and immobilizing a patient suffering from a spinal injury. The spineboards presently available generally comprise a flat plywood board formed with a plurality of slots arranged at spaced intervals about the periphery of the board. The slots are suitable for use as handles and mounting passages for straps for use in strapping the patient to the board. Two hardwood runners are fastened to the underside of the board to add strength and to support the board above a support surface in use. Generally, the patient restraining straps are belts of the type commonly used seatbelts in automobiles employing "Velcro" (T.M.) fasteners, rather than buckles.

The known spineboards do not provide for the mounting of the retraining straps closely adjacent the center of the width of the board with the result that they bridge the body of a patient and are not well suited to providing a body embracing restraint in the form of a sling which will encircle and secure the body of the patient with respect to the board.

Furthermore, the body restraining straps must be mounted at one or other of several set positions along the length of the board and do not make any provision for accurate adjustment. In addition, the known spineboards do not provide head restraining straps which serve to immobilize the head of a patient.

My spineboard has a number of features which can be used to advantage either independently of one another or collectively.

One of these features is the provision of a body restraint harness which has at least two lengths of flexible material, one end of each length being connected to the board at or adjacent the centre of the width thereof. Each length has a sufficient extent to extend from its point of connection to the board, around the body of a patient to be secured at its other end to the board. The two lengths can be extended about the patient in opposite directions thereby to provide oppositely acting slings which will serve to retain the patient's body against lateral movement with respect to the board.

A further feature of my spineboard is that a slipway is formed on the board and extends longitudinally of the board at the centre of the width thereof and the body embracing harness is slidably mounted in the slipway so as to be adjustable to any required position along the length of the board.

Yet another feature of my spineboard is that the slipway described in the preceding paragraph permits two body restraining harnesses to be mounted on the board, both of which are longitudinally adjustable so as to be positionable to encircle the body of the patient at any required position.

I have found that a convenient form of slipway is one where two mounting slots are formed adjacent the centre of the width of the board and extend longitudinally thereof.

I have found that by mounting the body restraining harness such that the distal ends of each length of retaining strap is secured closely adjacent the spine of a patient resting on the centre of the width of the board such that the two strap lengths may extend from opposite sides of the patient around the patient to encircle a major portion of the body of the patient in a sling-like manner thereby to immobilize the patient with respect to the board.

In addition, I provide a flange extending about the periphery of the board over which mounting hooks which are provided at the end of each restraining strap may hook in order to retain the restraining strap in a body encircling position.

In order to ensure that the patient's head is restrained against movement with respect to the spineboard, I provide a head restraint pad which is preferably of a triangular configuration and which has mounting straps at each corner arranged to cooperate with fasteners provided on the head rest portion of the support board arranged one above the head of the patient and one at each side of the neck of the patient in use.

To further restrain the patient against longitudinal movement with respect to the board, I provide shoulder straps which extend from the board through the armpit and around the shoulder of the patient to be secured to the board.

SUMMARY OF INVENTION

According to one aspect of the present invention, a spineboard comprises a body supporting board having a length and width proportioned to provide underlying support for a prostrate patient, a body restraint harness comprising at least two lengths of flexible material each having a proximal end retained on the board at or adjacent the centre of the width thereof, each length having a sufficient extent to extend from the proximal end in a first direction and around the body of a patient to be secured to the board at a point spaced from the proximal end in a second direction opposite said first direction whereby each length may form a body sling which extends in opposite directions about a patient.

According to a further aspect of the present invention, a spineboard comprises, a longitudinally elongated substantially rigid board having an upper support face, a slipway formed on said upper surface substantially centrally of the width thereof and extending longitudinally along a major portion of the length thereof, at least one patient embracing restraint slidably mounted in said slipway for longitudinal movement with respect to said board so as to be adjustable to accommodate injured patients of different height.

According to another aspect of the present invention, a spineboard comprises a substantially planner support board formed from a substantially rigid material, said board having a patient support surface and a lower face, said support board being proportioned and shaped to provide underlying support over the full length of the body of a prostrate patient, said support board having a side flange extending downwardly along at least each side of the support surface along at least a major portion of the length thereof to provide a mounting edge, a patient restraining belt having at least one free end, a mounting hook at each free end of said belt, said mounting hook being adapted to hook over said mounting edge to secure said belt and a patient about which the belt extends, in a stationary position with respect to said support board in use.

PREFERRED EMBODIMENT

The invention will be more clearly understood after reference to the following detailed specification read in conjunction with the drawings wherein:

FIG. 1 is a pictorial view of a spineboard constructed in accordance with an embodiment of the present invention.

FIG. 2 is a cross-sectional view of the spineboard of FIG. 1.

FIG. 3 is an enlarged detailed view of a fastener for the head restraint pad of FIG. 1.

FIG. 4 is a pictorial view of the underside of the spineboard of FIG. 1.

FIG. 5 is a pictorial view of the hook fastener at the end of the body restraining straps.

FIG. 6 is a sectional view of the belt tightening mechanism of the hook fastener assembly of FIG. 5.

Figure 7:
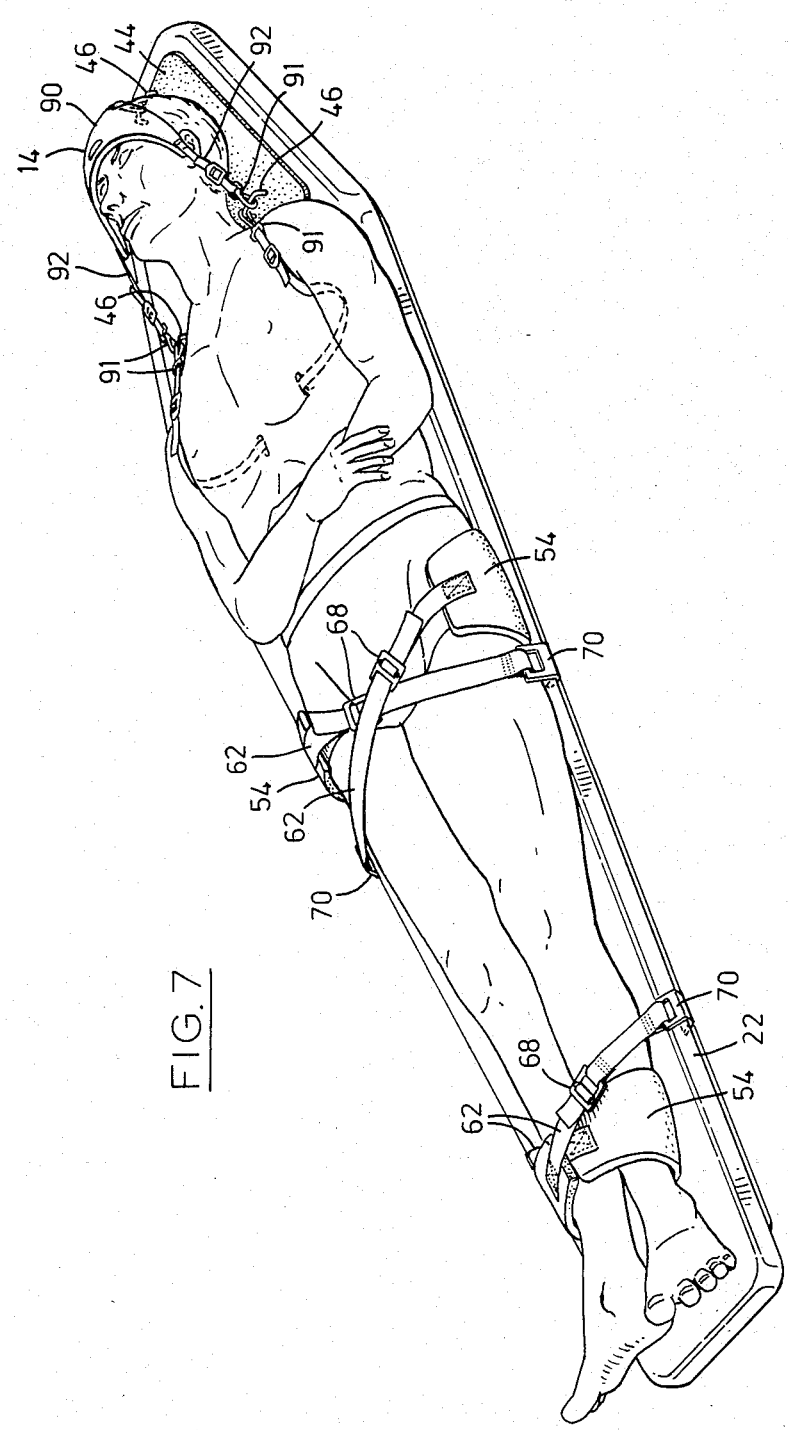
FIG. 7 is a pictorial view illustrating the manner in which a patient is immobilized on the spineboard of the present invention.

With reference to FIG. 1 of the drawings, the reference numeral 10 refers generally to a spineboard assembly constructed in accordance with an embodiment of the present invention. The spineboard assembly 10 consists of a spineboard 12, a head harness 14, a hip harness 16 and a leg harness 18.

The board 12 is formed from a substantially rigid plastic material such as fibreglass and includes an upper panel 20 which has a flange 22 projecting downwardly therefrom which extends about the entire perimeter of the panel 20. A central stiffening ridge 24 and side stiffening ridges 26 are formed on the underside of the panel 20. Air tight buoyancy chambers 28 are formed within the ribs 24 and 26 and have a sufficient capacity to ensure that the board is buoyant and will maintain a horizontal position when floating in a body of water. Panel 20 is shaped to provide a narrow plateau 30 which is located centrally of the width of the board and extends longitudinally from adjacent the foot portion 32 to the shoulder support portion 34. The plateau 30 has side edges 36 which extend downwardly to side panels 38 which extend to the flanges 22. Slots 40 are formed in the side edges of the plateau 30 and extend over the full length of the plateau. The slots 40 form a slipway along which the harnesses 14 and 16 may slide longitudinally relative to the board.

It is desirable to minimize the width of the plateau 30 in order to maximize the body encircling effectiveness of the body restraining harness, preferably the width of the plateau is about 4 inches in a board having a maximum width of about 18 inches.

The board 12 is formed with a shallow depression 42 at the head rest end thereof. A resilient head rest pad 44 is mounted in the recession 42. The head rest pad 44 is especially made from a non-absorbent neoprene rubber coated with a nylon skin. Three U-shaped brackets 46 are mounted on the board at the head rest end thereof and are secured by means of mounting screws 48 (FIG. 4). A pair of slots 50 open through the board in the shoulder support area 34.

The hip harness 16 and the leg hardness 18 are constructed in a like manner and differ only in their proportions. Like reference numerals are applied to like components of the harnesses 16 and 18. These harnesses include two lengths of flexible material each consisting of a resilient pad 54 and a belt 62. Each of the pads 54 has a flange 56 at the proximal end thereof which extends through the slots 36 on opposite sides of the plateau 30. The flanges 56 are formed with a plurality of eye-openings 58 through which a lace 60 is threaded to releaseably secure the flanges with respect to one another. The flanges 56 are sufficiently thin to be slidable along the slots 36. The pads 54 are sufficiently thick to ensure that they will not pass through the slots, thereby preventing lateral slipping of the harness through the slots 36. A belt 62 extends from the outer end of each pad 54 and is secured thereto by stitching 64 or the like. A belt retaining loop 66 is formed on the inner face of the pads 54. The belt 62 can be folded upon themselves and tucked into the loop 66 to be retained in a compact storage configuration.

Each belt 62 has a tightening buckle 68 and a mounting hook 70 located at the outer end thereof.

The tightening buckle 68 is best illustrated in FIGS. 5 and 6 of the drawings to which reference is now made. The buckle 68 has a roller 75 rotatably mounted on a shaft 77 which is slidably mounted on the buckle. A plurality of ridges 79 are formed on the roller 75. The end of the belt 62 is threaded around the roller 75 and can be tightened merely by pulling the belt tight. The tension in the belt pulls the roller 77 toward the end of the buckle 68 and locks the belt between the roller teeth 79 and the end of the buckle 68.

The hook 70 is mounted at the end of a strap 62a which is connected to the buckle 68. The hook 70 includes a first wall 72, a second wall 74 and a third wall 76 which are arranged in a generally U-shaped configuration to provide a mounting channel 78. The hook 72 is mounted on the end of the strap 62a in a conventional manner.

The harness 16 and 18 is proportioned such that it can be extended around the body of the patient and the hooks 70 may hook under the flanges 22 at any position along the length of the edge of the board as shown in FIG. 2 of the drawings. Thereafter, the strap 62 can be tightened to securly embrace the patient. By reason of the fact that the proximal end of each length of harness is retained at the slipway adjacent the centre of the width of the board, the two lengths act as slings which substantially encircle the body of the patient when the lengths are extended to opposite side edges of the board. This sling form of restraint substantially immobilizes the patient.

The shoulder harness is in the form of a belt 80 which is looped through the slots 50 formed in the shoulder support area 34 of the board. The belt 80 has a buckle 82 and fastener 84 connected to each end thereof. The buckle 82 and fastener 84 are best illustrated in FIG. 3 of the drawings. The buckle 82 is of a conventional slip type which permits movement of the belt 80 on support shaft 84 to effect tightening and loosening of the belt 80. A second strap 80a is mounted on the support bar 86 and is connected to a mounting ring 88 upon which a conventional safety hook 90 is mounted. By depressing the bar 92, it is possible to hook the hook 90 onto and off of the locking brackets 46.

The head restraint 14 consists of a pad 90 which is formed from a soft resilient material similar to that of the pads 54. The material is preferably neoprene rubber. Belts 92 are connected to each of the three corners of the pad 90 and each have a fastener assembly of the type illustrated in FIG. 3 of the drawings attached to the free end.

The pad 90 has a lower edge 94 which is formed with a concave curvature so that the pad 90 can extend over the forehead of the patient as shown in FIG. 7 of the drawings without covering the eyes of the patient. An opening 96 is formed in the pad 90 to facilitate deformation of the pad into the curved configuration required in use without buckling of the pad.

In use, the spineboard is maneuvered below a patient. When the patient is floating in a body of water, the spineboard is submerged below the patient and allowed to float upwardly to underly the patient. The patent is then positioned centrally of the width of the board with the head of the patient resting on the head rest pad 44. The shoulder straps 80 are then threaded beneath the arms of the patient and over the shoulders as shown in FIG. 7. The hooks 90 are secured to the brackets 46 and the straps 80 are tightened by pulling them through the buckles 82. By securing the shoulder harness, the patient is restrained against longitudinal movement with respect to the board.

The hip harness 16 is then located at the required position along the length of the board by sliding it longitudinally in the slots 46 as previously described. The straps 62 are then extended across the patient and the hooks 70 are hooked around the flanges 22 at the opposite edge of the board so as to embrace the patient at the hips. The straps 62 are then drawn tight through the buckles 68 as previously described. The leg harness 18 is positioned at the required position along the length of the board by sliding it along the slipway formed by the slots 36 as previously described and the straps 62 are fastened by means of the hooks 70 to the flanges 22 and the straps 62 are drawn tight as previously described.

The head strap assembly 14 is then secured as shown in FIG. 7 of the drawings with the pad 90 extending over the forehead of the patient and the safety hooks 91 hooked to the brackets 46. The straps 92 are tightened so as to draw the pad 90 against the forehead of the patient with a sufficient force to retain the patient's head and prevent relative movement of the patient's head with respect to the board.

From the foregoing, it will be apparent that the spineboard of the present invention is well adapted to secure a patient and render the patient immobile with respect to the spineboard so that the patient can be moved with a minimum of risk of additional spinal injury resulting from movement of the patient. The fact that the hip and leg embracing harnesses can be moved longitudinally of the board permits these harnesses to be positioned at an optimum position for any size patient. Furthermore, by reason of the fact that the hip and leg harnesses have their inner ends secured to the board closely adjacent the center of the width of the board, they have sufficient flexible extent to extend around the body of the patient in an embracing configuration closely conforming to the body contour and this serves to minimize the freedom of movement of the patient while providing a comfortable support.

Furthermore, by providing a shoulder harness which extends around the shoulders of the patient, longitudinal movement of the patient with respect to the board has been minimized with the result that if it is not possible to maintain the board in a horizontal position while transporting the patient, moving the board from the horizontal position will not result in excessive movement of the patient.

In addition, by providing a head harness which has a three-point connection including a connection centered above the head of the patient and connections locating on each side of the neck of the patient, it is possible to secure the head of the patient against movement with respect to the head rest by means of a head band which has fasteners which are positioned to be releasably connected to the fastening points.

By forming the stiffening ribs 26 and 28 so that they project a substantial distance below the lower edges of the flanges 22, these reinforcing ridges serve to support the board on an underlying surface with the flanges 22 spaced above the support surface a sufficient distance to permit the hooks 70 to hook under the flanges 22 without requiring that the board be moved. The gap which is provided below the flange 22 also permits manual engagement of the flange 22 for use as a handle when lifting the board. By reason of the fact the flange 22 extends about the entire periphery of the board, the hooks 70 can be positioned at any point along the length of the board and additional restraining straps can be extended across the board using hooks 70 for engaging the flanges 22 at opposite edges of the board.

As previously indicated, the board 12 is preferably made from a fibreglass material. The pads 54 are preferably made from neoprene rubber and the straps 62, 80 and 92 are preferably formed from a plastic material such as polypropylene.

Various modifications of the present invention will be apparent without departing from the scope of the invention. For example, the slipway may be in the form of a single slot located centrally of the width of the board with the proximal ends of each length of harness being enlarged to prevent passage through the slipway. In a further modification, a slipway may be formed centrally of the width of the board and a mounting rod may be mounted on the underside of the board to extend along the length of the board with the proximal ends of the length of harness being formed with an eye which is threaded over the rod to be slidably mounted thereon. It will also be apparent that while the recesses which are formed on either side of the raised plateau facilitate movement of the harness when a patient is resting on the board, the board may have a planner upper surface.

It will also be apparent that the proximal ends of each length of harness need not be secured with respect to one another but may be independently slidable along the length of the board so that a staggered aray of restraining belts may be located along the length of the body of the patient in use. These and other modifications of the structure of the present invention will be apparent to those skilled in the art.

I claim:

1. A spineboard comprising:
   (a) a body supporting board having a length and width proportioned to provide underlying support for a prostrate patient and a slipway formed substantially centrally of the width thereof, and extending longitudinally along a major portion of the length thereof,
   (b) a body restraint harness comprising at least two lengths of flexible material each having a proximal end mounted on the board at said slipway so as to permit longitudinal movement of said proximal ends with respect to the board while preventing lengthwise movement of the proximal ends of each end with respect to the board, each length having a sufficient extent to extend from the proximal end in a first direction and around the body of a patient to be secured to the board at a point spaced from the proximal end in a second direction opposite said first direction whereby each length may form a body sling which extends in opposite directions about a patient.

2. A spineboard as claimed in claim 1 wherein said slipway extends longitudinally along a major portion of the length thereof.

3. A spineboard as claimed in claim 1 wherein the proximal ends of oppositly disposed lengths of harness are interconnected.

4. A spineboard comprising:
   (a) a longitudinally elongated substantially rigid board having an upper support face formed to provide a raised spine support plateau which extends longitudinally along a major portion of the length thereof and is located centrally of the width thereof,
   (b) a slipway comprising a pair of passages formed in said board and extending transversely thereof beneath and longitudinally of said spine support plateau
   (c) at least one patient embracing restraint slidably mounted in said slipway for longitudinal movement with respect to said board so as to be adjustable to accommodate injured patients of different height.

5. A spineboard as claimed in claim 4 having two body embracing restraints slidably mounted in said slipway, for longitudinal movement with respect to said board, one of said body restraints being proportioned to encircle the hips and the other being proportioned to encircle the legs of a patient in use.

6. A spineboard as claimed in claim 1 wherein said board has a shoulder support area arranged to underly the shoulder of a person resting on said support face, and a pair of shoulder support straps mounted on said board, each shoulder strap having a sufficient length to extend upwardly from the board between the patient's arms and chest and around the patient's shoulder and means for releasably securing said shoulder straps in a shoulder encircling relationship with respect to said patient to secure the patient's shoulders with respect to the board in use.

7. A spineboard comprising:
   (a) a longitudinally elongated substantially rigid board having an upper support face formed to provide a raised spine support plateau which extends longitudinally along a major portion of the length thereof and is located centrally of the width thereof,
   (b) a slipway comprising a pair of passages formed in said board and extending transversely thereof beneath and longitudinally of said spine support plateau,
   (c) a first pair of body embracing restraints slidably mounted in said slipway, for longitudinal movement with respect to said board, one of said body restraints being proportioned to encircle the hips and the other being proportioned to encircle the legs of a patient in use, each of said restraints include two wide resilient pads, two belts and two buckles, the wide pads having their inner ends connected to one another beneath said spine support plateau, the belts extending one from each outer end of each wide pad and one of said buckles being located at the outer end of each belt, said buckles being securable to said board to retain said pads in the body encircling position about a patient in use.

8. A spineboard comprising:
   (a) a longitudinally elongated substantially rigid board having an upper support face formed to provide a raised spine support plateau which extends longitudinally along a major portion of the length thereof and is located centrally of the width thereof,
   (b) a slipway comprising a pair of passages formed in said board and extending transversely thereof beneath said spine support plateau along a major portion of the length thereof,
   (c) two body embracing restraints slidably mounted in said slipway, for longitudinal movement with respect to said board, one of said body restraints being proportioned to encircle the hips and the other being proportioned to encircle the legs of a patient in use,
   (d) said board being formed with locking flanges at opposite sides thereof, said flanges being at least co-extensive with said slipway, said flanges extending downwardly from said support face and having an outer edge, said patient embracing restraint comprising a belt having at least hook shaped buckle adapted to hook over said outer edge of said flange to retain said restraint with respect to said board.

9. A spineboard as claimed in claim 8 wherein said board has a lower face and wherein a pair of stiffening ribs are formed on said lower face, said stiffening ribs extending along each side edge of said board laterally inwardly of and adjacent of one of said flanges, said stiffening ribs having a height which is greater than the depth of said flange whereby the ribs form rails which will support the board on an underlying surface with the outer edges of the flanges spaced above the surface to provide access to permit a hook to pass under the outer edge of the flanges when the board is supported by the support rails.

10. A spineboard comprising:
    (a) a longitudinally elongated substantially rigid board having an upper support face formed to provide a raised spine support plateau which extends longitudinally along a major portion of the length thereof and is located centrally of the width thereof,
    (b) a slipway comprising a pair of passages formed in said board and extending transversely thereof beneath said spine support plateau along a major portion of the length thereof,
    (c) two body embracing restraints slidably mounted in said slipway, for longitudinal movement with respect to said board, one of said body restraints being proportioned to encircle the hips and the other being proportioned to encircle the legs of a patient in use,
    (d) said board being formed with a lower face on which a first stiffening rib is formed, said stiffening rib underlying said spine support plateau and extending longitudinally thereof.

11. A spineboard as claimed in claim 10 wherein said board has two additional stiffening ribs located on said lower face, said additional ribs being located one adjacent each side edge of said board.

12. A spineboard as claimed in claim 11 wherein said ribs are hollow and form buoyancy chambers of sufficient capacity to make the board horizontally buoyant in water.

13. A spineboard comprising:

(a) a body supporting board having a length and width proportioned to provide underlying support for a prostrate patient, said board has a head rest portion on one end thereof, head rest fastener means on said head rest portion, said head rest fastener means being arranged one at each corner of a triangular array so as to provide one fastener above the head and one fastener at each side of the neck of an injured patient supported by the board in use, (b) a triangular shaped head restraint pad proportioned to fit over the head of an injured patient, said pad having securing straps connected to each corner thereof, a fasteners on each securing strap adapted to releasably engage said fastener means of the head rest portion whereby the head restraint pad may engage the head of a patient resting on the board and hold the patient's head stationary with respect to the board, (c) a body restraint harness comprising at least two lengths of flexible material each having a proximal end retained on the board at or adjacent the centre of the width thereof, each length having a sufficient extent to extend from the proximal end in a first direction and around the body of a patient to be secured to the board at a point spaced from the proximal end in a second direction opposite said first direction whereby each length may form a body sling which extends in opposite directions about a patient.

* * * * *